(12) United States Patent
Lee

(10) Patent No.: US 8,455,263 B2
(45) Date of Patent: *Jun. 4, 2013

(54) QUANTITATIVE ANALYTE ASSAY DEVICE AND METHOD

(76) Inventor: Jin Po Lee, Carlsbad, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 12/317,814

(22) Filed: Dec. 30, 2008

(65) Prior Publication Data

US 2010/0167264 A1 Jul. 1, 2010

(51) Int. Cl.
*G01N 33/558* (2006.01)

(52) U.S. Cl.
USPC ............... 436/514; 422/420; 422/425; 435/5; 435/7.23; 435/7.21; 435/7.32; 435/7.9; 435/287.7; 435/287.9; 435/805; 435/810; 435/970; 436/64; 436/65; 436/525; 436/531; 436/164; 436/169; 436/172; 436/805; 436/810; 436/811; 436/813; 436/814; 436/818

(58) Field of Classification Search
USPC 436/514, 518, 810; 435/7.1, 7.94; 422/287.1, 422/287.2, 287.7, 287.9
See application file for complete search history.

(56) References Cited

U.S. PATENT DOCUMENTS

| | | | |
|---|---|---|---|
| 5,384,264 A | 1/1995 | Chen et al. | |
| 5,821,073 A | 10/1998 | Lee | |
| 6,528,323 B1 * | 3/2003 | Thayer et al. | 436/518 |
| 7,175,992 B2 | 2/2007 | Fong | |
| 2003/0119203 A1 | 6/2003 | Wei et al. | |
| 2005/0112780 A1 | 5/2005 | Song | |
| 2006/0246513 A1 | 11/2006 | Bohannon | |
| 2007/0087451 A1 | 4/2007 | Kirkegaard et al. | |
| 2008/0125582 A1 | 5/2008 | Millan | |

FOREIGN PATENT DOCUMENTS

| | | |
|---|---|---|
| EP | 1 879 028 A1 | 1/2008 |
| WO | WO 88/08534 * | 11/1988 |
| WO | WO-00/31539 | 6/2000 |

OTHER PUBLICATIONS

Extended European Search Report dated Feb. 4, 2013 in related European Patent Application No. 09836476.3.
Geertruida, et al., "Lateral flow (immuno)assay: its strengths, weaknesses, opportunities and threats. A literature survey," Anal. Bioanal. Chem., (2009), 393:569-582.
International Search Report and Written Opinion in related PCT Patent Application No. PCT/US09/06297.

* cited by examiner

*Primary Examiner* — Chris L Chin
(74) *Attorney, Agent, or Firm* — Foley & Lardner LLP

(57) ABSTRACT

The present invention relates to an assay device and a method for using such for the quantitative determination of an analyte, based on a test strip, which contains a porous test membrane allowing for capillary flow of the analyte and complexes of the analyte, a porous upstream membrane in fluid connection with the test membrane and a porous downstream membrane in fluid connection with the test membrane, wherein the test membrane contains a test site having immobilized thereon a ligand capable of reacting with the analyte and binding such to the test site, and two standard band sites having immobilized thereon known high and low concentrations of a calibrator agent capable of reacting with a label conjugate and binding such to the standard sites, wherein the upstream membrane has a site for the application of a sample to be analyzed, and has a site downstream from the sample application site for depositing label conjugates capable of reacting with the analyte and label conjugates capable of reacting with the immobilized calibrator agents in the standard bands to provide a known label response in the standards bands, and the downstream membrane is capable of absorbing said sample and providing the capillary flow for the sample through the upstream and test membrane.

13 Claims, No Drawings

QUANTITATIVE ANALYTE ASSAY DEVICE AND METHOD

FIELD OF INVENTION

The present invention relates to methods and devices for assaying biological fluid samples and particularly bodily fluid samples. More particularly the invention relates to methods and devices for detecting and quantitatively measuring the concentration of an analyte in a sample.

BACKGROUND

Quantitative analysis of fluid samples including antigens, antibodies hormones, and other secreted proteins as well as other types of proteins frequently provides critical diagnostic data. The concept of immunoassays is well known in the art and is based on reagent impregnated capillary membranes in which an immobilized reagent in the detection zone of the strip binds to analytes conjugated with visual label such as a latex particle or metal containing compounds. In addition U.S. Pat. Nos. 3,654,090, 3,791,392 and 3,817,838 disclose enzyme labels and the means to detect such, and U.S. Pat. No. 4,062,733 discloses radioactive labels. Preferred labels are derived from metal sols. Labels such as prepared from a gold sol are bound to a ligand capable of further binding or conjugating to an analyte or other ligand or antibody. Test strips have been used in qualitative assays in a large number of applications involving analytes contained in such bodily fluids as urine and blood. Probably the earliest and most common use of assays is in detecting human chorionic gonatropin as an indicator of pregnancy in humans. These assay devices are based on test strips where the assay is performed and results read in a single step, e.g. where the liquid sample is placed onto a porous membrane, any analyte of interest therein binds a corresponding ligand, and the results are indicated visually in a detection zone separate from the sample loading zone through formation of a specific complex. The test strips are normally contained in a dipstick or cassette allowing the user to conduct the test without any additional equipment. Such devices are disclosed in U.S. Pat. Nos. 4,235,601, 4235,601 and 5,384,264. Assay devices that can be used with whole blood are disclosed in U.S. Pat. No. 5,821,073.

Known assay devices generally involve a sandwich assay or a competitive assay In a sandwich assay, analyte of interest present in a fluid sample interacts with a ligand bound label or tracer resulting in a complex of analyte and label. This can occur prior to adding the analyte to the test strip or the label bound ligand can be removably deposited on the porous membrane forming the test strip. The test strip allows the label-bound analyte to move by capillary action to a sample capture zone where the analyte complex is retained by virtue of being bound to the immobilized capture ligand normally an antibody to the analyte. In the case of a gold label the presence of the analyte is indicated by color formation at the analyte test zone. Preferably the assay device also contains a second immobilized ligand band, generally identified as a control band capable of binding to label ligand even in the absence of an analyte, to show that the strip is functioning properly.

In a competitive or inhibition assay both the analyte and the label ligand are capable of reacting with the immobilized ligand in the sample capture zone and thus both the analyte and the label bound ligand compete for attachment to the immobilized ligand in the sample capture zone. Any analyte present would displace the binding of a labeled ligand. The presence of a signal in the sample capture zone would thus indicate a negative result.

Most of the assay devices based on test strips determine the presence or absence of an analyte but do not provide but a very rough measure of the quantity of an analyte present in fluid sample. Even those that give a quantitative measurement by incorporating a standard in the test device suffer from inaccuracies resulting from temperature, air moisture, flow variations, strip to strip variations and signal strength variations. These and other deficiencies of the prior art assay devices are overcome by the chromatographic assay device of the present invention, which provides a rapid effective, and efficient quantitative analysis of fluid samples.

SUMMARY OF THE INVENTION

The present invention provides an assay device for and a method of measuring the amount of an analyte in a fluid sample using a solid phase chromatographic assay, such as a sandwich assay, in which one or more analytes of interest is bound to a label conjugate and is also bound to a capture reagent in a test band as part of a specific binding pair. In addition to the test band, the devices of the present invention contain standard bands of immobilized calibrator agents capable of binding to label reagents and employ such labeled reagents captured at the standard bands by the calibrator agents to create a template against which to measure the concentration of an analyte in a sample bound in the test band. The immobilized calibrator agents in the standard bands are contacted with the corresponding label reagents as the fluid sample passes through the assay strip. Any analyte of interest present in the fluid sample is bound at the sample capture band. Based on the relative intensity of the label bound in these bands an accurate concentration of analyte can be obtained. Thus the density or intensity of a label such as a gold sol conjugate in the various sample capture bands on the membrane strip reflects the amount of the analyte present as do the standard bands which then reflect the density of the calibrator agent bound and which has a known concentration. Thus commercially available optical readers can convert the reflected light intensity of the sample into concentration as measured on the basis of the curve derived from the reflected intensity of the standard bands of known concentrations.

The present invention comprises a lateral flow assay method and system including a test strip and/or a cassette for holding the test strip, for determination of the presence and/or quantity of analytes in samples, including but not limited to biological or other samples containing materials including antigens, antibodies, hormones and other secreted proteins, cell surface proteins, transmembrane proteins, glycoproteins, enzymes, proteins associated with cells and other proteins, proteins associated with pathogens such as bacteria, viruses, and fungi, carbohydrates, drugs, peptides, toxins, nucleic acids, small molecules, and aptamers. This novel assay or system can detect and/or quantitate analytes in small volumes of samples. Generally, the sample volume is less than about 100 µl. Most preferably, the sample volume is about 40 µl. This assay or system can also separate cells from fluid in a sample, such as red blood cells or white blood cells or other cell types. The assay or system also provides low background noise and is highly efficient.

DETAILED DESCRIPTION OF INVENTION

For ease of understanding, the following definitions will apply throughout this description:

1. The term "antigen" as used herein refers to any analyte, which is capable of binding antibodies. Antigens may comprise, without limitation, chemical compounds, polypeptides, carbohydrates, nucleic acids, lipids, and the like, including viral particles, viral subunits, bacterial and parasite surface antigens, and host proteins that may be diagnostic of the subject's condition.

2. A "binder" refers to a ligand for the analyte as in the format of a sandwich assay, or a ligand for both the analyte and the tracer or label as in the format of a competitive assay A binder can be chosen from a group of molecules or compounds capable of binding the analyte, such as an antigen to the antibody analyte, or an antibody to the antigen analyte.

3. A "test zone or band" refers to an area in which a binder or the analyte is attached, movably or immovably, such as to the analyte test strip portion of an assay device.

4. The term "test strip" or "assay strip" refers to a porous membrane capable of capillary flow of the fluid sample containing the bound analytes and other antigens involved in the determination of the analyte concentration. Common porous membranes are fiberglass, porous nitrocellulose or polyethylene. An "analyte test strip" of the invention consists of, collectively, all of the zone supporting membranes and any filters of the assay device.

5. A "tracer" refers to a ligand for the analyte or the binder labeled with a detectable label, preferably a visually readable particulate label, such as colloidal gold, latex and liposomes including dye, carbon black, and the like.

6. A "sample loading or application zone" refers to an area of an analyte test strip on which a fluid analyte sample is applied for migration to the test bands.

7. A "fluid analyte sample" can be any fluid suspected of containing analyte of interest for which a particular assay is specific. Test sample may represent any body fluid, including urine, blood, sweat, lymph, intraperitoneal fluid, crude tissue extract or homogenate, derived from a fetus, neonate, juvenile or adult subject; a non-biological fluid such as water from some ecological niche, e.g., a river or a lake; or a solution used in a laboratory.

8. A "label" is a molecule or compound, which directly or indirectly mediates the formation of a signal (such as a color change), which is used in assay to indicate the presence, absence or concentration range of analyte of interest in a test sample. Labels may include enzymes, fluorescers, liposomes, erythrocyte ghosts, polymer microcapsules, color polymer particles (latex), and preferably includes sols of metal-containing compounds. A wide variety of patents and patent applications provide an extensive literature of different techniques for producing detectible signals in immunoassays. The following list of United States patents is merely illustrative of the type of label which can find application in this invention: U.S. Pat. No. 3,646,346 discloses radioactive labels; U.S. Pat. Nos. 3,654,090, 3,791,932, and 3,817,838 disclose enzyme labels; U.S. Pat. No. 3,996,345 discloses fluorescer-quencher labels; U.S. Pat. No. 4,062,733 discloses radioactive label; U.S. Pat. No. 4,067,959 discloses fluorescer or enzyme label; U.S. Pat. No. 4,104,099 discloses chemiluminescent label; and U.S. Pat. No. 4,160,645 discloses non-enzymatic catalyst label. U.S. Pat. No. 3,966,879 discloses an electrophoretic technique employing an antibody zone and U.S. Pat. No. 4,120,945 discloses a radioimmune assay (RIA) where labeled analyte is initially bound to a solid support through antibody. U.S. Pat. No. 4,233,402 discloses enzyme pair labels; U.S. Pat. No. 4,720.450 discloses chemically induced fluorescent labels; and U.S. Pat. No. 4,287,300 discloses enzyme anionic charge labels. Labels can also be metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and preferably include colloidal gold in dry form.

"Label response" refers to the signal strength that is generated by the label when it becomes attached to the reagents immobilized in the test or standard bands. With color generating labels reflective light units are a preferable way of measuring label response.

9. A "complex" means (depending on the context) any multimolecular complex formed by analyte and one or more ligands, or by labeled ligand and immobilized ligand. In a sandwich-type immunoassay, e.g., the following complexes occur: analyte/labeled ligand duplex first produced in the assay (first complex) and analyte/labeled ligand/immobilized ligand triplex formed second in the assay (second complex).

10. "Fluid communication" refers to structures which are in contact with, but not necessarily affixed to one another and which allow the passage of a fluid from one to the other.

11. "Assay" refers to several different types of assay formats in which an analyte of interest can be detected using an assay analyte test strip. For example, in a sandwich-type immunoassay, analytes of interest in the analyte sample, when present, bind a labeled tracer movably incorporated in the analyte test strip (consisting of a porous membrane) at the tracer zone to form a first complex. The tracer is a molecule, which binds the analyte of interest and is conjugated to a label, preferably a metal label, and most preferably colloidal gold.

12. The term "capture band" or "capture site" as used herein refers to a region or zone on the chromatographic assay strip that contains at least one analyte binding agent. The analyte binding agent is usually immobilized in a band or zone such that after reaction with a detectable agent, the band or zone produces an observable or measurable result reflecting the presence or amount of analyte present in the sample. The "capture band" may be comprised of more than one capture zone for capturing more than one analyte in the sample, in which event, more than one analyte binding agent may be used. For example, two assay combinations that are considered to be within the scope of the invention are assay combinations that simultaneously detect hepatitis C virus. (HCV) and human immunodeficiency virus (HIV), and assay combinations that simultaneously detect Hepatitis B surface antigen (HBsAg) and *Treponema pallidum* antigen (TP). Still other combinations are possible and are within the scope of the invention.

13. The term "conjugate" and "detectable agent" are used interchangeably herein to refer to an antibody or an antigen that is conjugated to a detectable material such as a colored agent, a fluorescent agent, an enzyme agent or a chemiluminescent agent. In the practice of the present invention, the "conjugate" or "detectable agent" specifically binds the analyte to be determined or the captured analyte immobilized on the capture band Optionally, the "conjugate" or "detectable agent" produces a measurable quantitative reading at the capture band that reflects the amount of an analyte present at the capture band. As described further below, the direct measurable quantitative density in the capture band does not necessarily reflect the amount of an analyte present at the capture band through binding, but the intensity of band as measured by reflective light units (RLU) does reflect the amount of an analyte present at the capture band.

14. The term "standard band" as used herein contains calibrator agents immobilized in calibrator binding zones on the test strip. The calibrator agents bind specifically to calibrator binding agents to form a calibrator binding pair. The present invention includes two calibrator bands. An advantage to having calibrator binding pairs is that they act as internal calibrators, that is, the calibrator against which the amount of an analyte present at the capture band may be calculated. The calibrators may be used to correct for strip to strip variability. One of the calibrators can be designated a high calibrator ("HC") and the other of the calibrators can be designated a low calibrator ("LC"). Additionally, the reflection density of HC and of LC, can be used to determine the standard curve. The standard curve is made for each quantitative assays by using the RLU values of the calibrator agents to generate a regression equation to describe the relationship between two variables. Although, in general, any conventional calibrators can be used herein, it is generally preferred to use as calibrators compounds that do not exist in the sample or do not immunologically cross-react with compounds that exist in the sample; for example, 2,4-dinitrophenylated bovine serum albumin (BSA-DNP), which can be purchased from Molecular Probes (Eugene, Oreg., cat# A-23018) can be used as the calibrator reagent. The compound 2,4-dinitrophenol (DNP) is a small molecule which does not exist within the human body but acts as a hapten; that is, it is immunogenic when conjugated to a larger molecule such as a protein carrier and injected into an antibody-producing mammal such as a mouse, a rat, a cow, a rabbit, a horse, a sheep, or a goat.

The test devices of the present invention comprise test strips, which may be enclosed in a cassette for easier use. Such test strips enclosed in such cassettes are described in U.S. Pat. Nos. 5,821,073 and 5,384,264, the disclosures of which are hereby incorporated by this reference. The test strips employed in the present invention generally comprise a porous test membrane of sufficient porosity to allow the components of the test including the analyte and its complexes to flow through the membrane by capillary action. Preferred membranes are porous nitrocellulose, porous. polypropylene and paper membranes. Such membranes are well known in the art. These membranes contain immobilized ligands capable of binding the analyte in a test zone, preferably in the form of a band across the width of the test membrane as well as the HC and LC calibrator agents in separate zones across the width of the test membrane in the calibrator are standard bands. As indicated the immobilized ligands used for the test and calibrator zones are different. Known amounts of calibrator agents are immobilized in the standard bands to establish the base line for the quantitative determination of the analyte. The remaining active sites after the application of the ligands in the various zones on the membrane are blocked to allow free flow of the analyte, analyte complexes, labeled ligands and labeled ligand complexes through the test strip.

In addition to the porous membrane the test strips of the present invention contain a second porous membrane upstream from the first membrane but in fluid communication with the test membrane containing the immobilized ligand bands. The upstream membrane is of an inert type in that it does not contain sites, which would bind ligands flowing through the membrane. Such membranes are preferably made of unwoven fiberglass or polypropylene, again of sufficient porosity to allow capillary flow of analyte, analyte complexes and labeled ligands. These membranes can also be suitably used to separate the analyte to be tested from components in the sample, which could interfere in the analysis of the analyte. Thus in the analysis of blood the red and white blood cells can be separated from the fluid serum containing the artalyte to be tested. The upstream membrane therefore contains a site for the application of the sample, and in addition contains the labeled ligands, downstream from the application site and upstream from the contact with the test membrane, that react with the analyte in a sandwich assay or with the bound ligand in the test zone in a competitive assay, as well labeled ligands that complex with the bound calibrator ligands in the standard bands. The labeled reagents are deposited on the upstream membrane in a manner that they can lift of from the membrane when contacted by the fluid sample and in the case of the analyte react with the analyte to form a complex that can then continue to flow from the upstream membrane into the test membrane.

The test strip further contains a third membrane, in fluid connection with the test membrane, at the downstream end of the test membrane capable of absorbing the fluid sample that has passed through the test membrane and that acts as the driving force to cause the fluid sample to flow through the test membrane by capillary action. Such adsorption pads are preferably made of high absorbency materials such as paper that are capable of absorbing the sample and any buffer added to the strip.

The operation of the assay of the present invention basically involves the addition of a known quantity of a fluid sample containing a suspected analyte to the device at the sample application site using a transfer pipette. Generally the amount of sample will be in the range of 10 to 100 microliters. Usually when the test strip is incorporated into a cassette, a sample well is provided for the addition of the sample to the test strip. The sample is absorbed by the upstream membrane and drawn by capillary action through such upstream membrane towards the test membrane. In the process the sample passes through the region of the upstream membrane where label bound ligands are removably deposited. In addition to the label ligand that binds to the analyte if present the upstream membrane also contains known amounts of the high and low calibrator ligand removably deposited on the upstream membrane.

In the case of the sample being blood the upstream membrane can also act as a filter to filter out the red and white blood cells but let the serum pass through. The flow of the sample through the test strip is frequently facilitated by the addition of a buffer. In general the amount of buffer added is at least equal to but no more than five times the quantity of the fluid sample. Suitable buffers include any pharmaceutically acceptable aqueous buffer, which will not react with the test sample of the other test and control ligands of the test strip. In general phosphate buffers, based on mono and di sodium hydro phosphate and commercially available, are preferred although other buffers such as citrate buffers or Ringer's solution may also be used.

The sample stream picks up the label ligands for both the test and standard bands before contacting the test membrane. The preferred labels of the present invention are those that give rise to color complexes in the test and standard bands. Although color resulting from enzyme bound ligands or latex bound ligands which have been used in conjunction with qualitative assays using capillary flow of test strips such as disclosed in the above mentioned patents and others can be used in the assays of the present invention, the preferred color forming ligands are gold conjugates that can bind to the desired analyte to be analyzed and to the calibrator agents. The quantitative assay of the present invention is based on the color intensity of an analyte sample and the color intensity generated by the calibrator agents in the standard bands. Thus the higher the amount of analyte in the test sample, the more label ligands bind to the analyte and the higher the amount of label ligand/analyte complex that will bind to the to the immobilized ligand in the test zone, increasing the label intensity in the band. Thus label intensity increases with increasing amount of analyte present in the sample. However in order to accurately establish the actual concentration of the analyte, factors other than analyte concentration must be excluded from any quantitative determination. It is for that purpose that the test strips of the present invention employ the calibrator agents in the standard bands which then provide the means for an accurate quantitative determination. Preferably and for higher accuracy the present invention employs two calibrator agents in separate standard zones, before and after the test zone on the test membrane. Since a fixed amount of the calibrator agent is immobilized in the standard zones and an excess of the calibrator label conjugate is deposited in the upstream band, the same intensity of color is generated in the standard bands at any given time interval time during the test for different test strips made in the same way. Using the relative light units a standard curve can be obtained for each high and low calibrator zone, which then serves as the base for the determination of the quantitative amount of analyte present. Although, in general, any conventional calibrators can be used herein, it is generally preferred to use as calibrators agents that do not exist in the sample or do not immunologically cross-react with compounds that exist in the sample; for example, 2,4-dinitrophenylated bovine serum albumin (BSA-DNP), which can be purchased from Molecular Probes (Eugene, Oreg., cat# A-23018) can be U.S.ed as the calibrator reagent. The compound 2,4-dinitrophenol (DNP) is a small molecule which does not exist within the human body but acts as a hapten; that is, it is immunogenic when conjugated to a larger molecule such as a protein carrier and injected into an antibody-producing mammal such as a mouse, a rat, a cow, a rabbit, a horse, a sheep, or a goat. Immobilized ligands in the low calibrator standard zone are for example bovine thyroid globulin (BTG) antibodies and immobilized ligands in the high calibrator standard zone are for example goat anti-rabbit proteins. Conjugates used with the immobilized ligands are BTG gold antigens and rabbit IgG gold antigens.

In order to determine the amount of the analyte present it is necessary to develop the relationship of color intensity in the test zone with concentration of analyte in a sample. Such relationship, plotted as a curve, is obtained by preparing a solution or dispersion of the analyte to be tested at a known high concentration and then continuously diluting the test solution or dispersion and measuring the change in color intensity in exposed test strips. Obviously this curve will also be different at different time intervals. However these curves can be correlated with the standard curves obtained from the calibrator agents for known concentrations in the case of measurement of a sample containing an unknown amount of analyte. Thus in each test of an unknown sample three different color intensities are obtained. The intensities of the standard band can be correlated to the standard concentration curves for the analyte and a quantitative value for the analyte in the sample to be tested calculated. For verification purposes it is desirable to obtain relative light units for two exposure times, which can be correlated to the standard values of concentration vs. label response in reflectance units to obtain a verification of the concentration of the analyte in the sample.

In a simplified version of the quantitative assay of the present invention it is possible to immobilize known concentrations of the analyte as the calibrator in the standard bands. In that event only an excess of a single label ligand is required to be removably deposited in the upstream membrane receiving the sample. Thus a sample containing the analyte disperses the removably bound label ligand and allowing the analyte to react with the ligand to form a complex. The complex and excess label ligand are carried by capillary flow to the test membrane where analyte bound label ligand complex reacts with the immobilized antibodies and is captured to give a label response, which is preferably in the form of a color. Excess label ligand is then available to react with the known quantities of immobilized analyte in the standard zone to give a standard color intensity response. Based on pre-established color response to analyte concentration and the response provided by the calibrator in the standard bands, the concentration of the analyte in the sample can be established.

Although the necessary calibration of the standard strips and concentration calculations can be carried out manually, they are preferably embodied in software that can be read by commercial equipment capable of measuring the color intensity of the test band and the standard bands. The color intensity data points generated by the standard bands and known concentrations of analyte in the test band can be incorporated into a memory device such as an electromagnetic card or an rfid card. When such card is inserted into a commercially available optical reader, such as manufactured by Kaiwood Technology Co. together with a cassette that has been treated with a sample, the reader can provide the concentration of any analyte in the sample.

In general analytes and the corresponding complex forming antibodies, or antigen if the analyte is an antibody, are known in the art from the development of qualitative assays for such analytes, as are the label conjugates that will bind to the analyte. For example, if the lateral flow assay is intended to measure hepatitis B virus ("HBV") surface antigen (HBsAg) in a blood sample, the capture band will contain antibody to HBsAg immobilized on the test membrane at the test band.

Suitable analytes include, but are not limited to antigens, antibodies, hormones, drugs, cell proteins, DNAs, cardiac markers, tumor or cancer markers, autoimmune disease markers, or any macromolecule that could raise antibodies. When the analyte is an antigen, the antigen can be an antigen associated with an infectious agent. The infectious agent can be a virus, a bacterium, a fungus, or a prion. When the infectious agent is a virus, the virus can be selected from the group consisting of HIV, hepatitis virus A, B, C, and D, herpes simplex virus, cytomegalovirus, papilloma virus, Ebola vir, SARS virus Rhinovirus, and Vaccinia virus, but is not limited to those viruses. When the infectious agent is a bacterium, the bacterium can be a gram-positive bacterium or a gram-negative bacterium. The bacterium can be selected from the group consisting of *Bacillus anthracis, Escherichia coli, Helicobacter pylori, Neisseria gonorrheae, Salmonella* species, and *Shigella* species, but is not limited to those bacteria. When the infectious agent is a fungus, the fungus can be a *Mycosporum* species or an *Aspergillus* species, but is not limited to those fungi.

When the analyte is a hormone, typically it is selected from the group consisting of hCG, thyroxin, TSH, glucagons, insulin, relaxin, prolactin, luteinizing hormone, melanotropin, somatotropin, follicle-stimulating hormone, gastrin, bradykinin, vasopressin, and other releasing factors; however, other hormones of physiological or pathological interest can be the analyte.

When the analyte is a cancer or tumor marker, typically it is selected from the group consisting of prostate specific antigen (PSA), carcinoembryonic antigen (CEA), and α-fetoprotein; however, other cancer or tumor markers can be the analyte. When the analyte is a cardiac marker, the cardiac marker is typically selected from the group consisting of Troponin-I, Troponin T, Creatine kinase-MB isoforms (CK-MB), myoglobin, C-reactive protein (CRP), fatty acid binding protein (FABP), glycogen phosphorylase isoenzyme BB (GPBB), B-type natriuretic peptide (BNP) and pro-BNP; however, the analyte can be another cardiac marker. The invention is further illustrated but not limited by the following example.

EXAMPLE 1

Onto a test strip comprising a porous nitrocellulose strip as the test membrane sufficient human prostrate specific antigen (PSA) is immobilized in two standard bands to give rise to a color intensity when complexed with a gold label monoclonal psa specific antibody corresponding to a psa concentration of 1 and 10 nanogram per milliliter respectively. Furthermore PSA specific monoclonal antibodies are also deposited in the test band of the nitrocellulose strip. The bands are arranged such that the sample first contacts the low calibrator band showing the color intensity with the gold conjugate corresponding to 1 ng/ml of PSA antigen, then the test band, followed by the high calibrator agent band, capable of binding the equivalent of 10 ng/ml of PSA. The deposited antigen and the antibody in the bands are allowed to react with the epitopes on the nitrocellulose and become permanently immobilized in the standard and test bands on the test membrane. The remaining epitopes are then blocked using standard techniques. The correlation of the color density with analyte concentration and test time for the particular test strip is loaded into a memory card.

The test membrane is in fluid connection with an upstream non-woven fiberglass membrane onto which is deposited the antibody to the psa antigen conjugated to a gold label by techniques known in the art. The label conjugate is deposited down stream from where the sample to be analyzed is added to the upstream fiberglass membrane. The assay test strip also contains a sample absorption pad in fluid connection with the downstream end of the test membrane. The test strip is inserted into a cassette such as described in U.S. Pat. No. 5,821,073.

One drop of blood suspected of containing the psa analyte, approximately 30 microliters, is added to the sample applicator site on the upstream fiberglass membrane followed by one drop, about 40 microliters, of a commercially available phosphate buffer. The fiberglass membrane is sufficiently dense to filter out the red and white blood cells but will let the serum pass. The serum of the blood combined with buffer flows through the upstream membrane by capillary action to the label conjugate redistributing the gold antibody conjugate which then forms a complex with any analyte present in the sample. The buffer diluted serum passes from the fiberglass membrane to the porous nitrocellulose membrane and continues to flow by capillary action through the nitrocellulose membrane. Analyte gold conjugate complex is captured by the psa antibody deposited in the test band and gives rise to a reddish color the intensity of which corresponds to the amount of analyte present in the sample. Excess gold conjugate is also captured by the high and low standard bands containing sufficient calibrator agent to capture the equivalent of either one or ten ng/ml of analyte. In the presence of PSA analyte in the sample three bands of differing color intensity are obtained. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The reader employed, CHR 100, is manufactured by Kaiwood Industries, is capable of converting the color intensity into concentration using the data on the memory card. Color intensities were measured 10 and 15 minutes after the addition of the sample and buffer. The following results are obtained:

10 minutest test result

| Analytes | PSA Concentration | RLU |
|---|---|---|
| Calibrator H | 10 ng/ml | 10 |
| Calibrator L | 1 ng/ml | 1 |
| Sample | X | 4.04 |

Based on the two point standard curve, the reader showed 4 ng/ml of the psa antigen (X) in the sample.

| Analytes | PSA Concentration | RLU |
|---|---|---|
| Calibrator H | 10 ng/ml | 23.9 |
| Calibrator L | 1 ng/ml | 10.3 |
| Sample | X | 19.49 |

Based on the two point standard curve, the reader showed 4 ng/ml of psa antigen (X) in the sample.

The invention claimed is:

1. An assay device for quantitative determination of an analyte in a sample, comprising a test strip containing a porous test membrane allowing for capillary flow of the analyte, a porous upstream membrane in fluid connection with and located upstream from the test membrane and a porous downstream membrane in fluid connection with and located downstream from the test membrane,
    (a) the test membrane containing a test site having immobilized thereon a ligand capable of reacting with the analyte and binding the analyte to the test site, a first standard band having immobilized thereon a first calibrator agent corresponding to a first known concentration of analyte, and a second standard band having immobilized thereon a second calibrator agent corresponding to a second known concentration of analyte, wherein each of the first and second calibrator agents are capable of reacting with different label conjugates and binding the label conjugates to the first and second standard band sites to produce a measurable response,
    (b) the upstream membrane having a sample application site to which the sample is applied, and having a label conjugate site downstream from the sample application site having the label conjugates deposited thereon, and
    (c) the downstream membrane capable of absorbing the sample and providing the capillary flow for the sample through the upstream membrane and the test membrane.

2. The assay device of claim 1 the label conjugates on the upstream membrane produce a measurable response measured as a color.

3. The label conjugates of claim 2 comprising gold conjugates, fluorescent dye conjugates, latex conjugates and enzyme conjugates.

4. The device of claim 1 wherein the test strip is contained in a cassette allowing for the addition of the sample at the upstream membrane and viewing the results of color formation at the sites of the test membrane.

5. A method for quantitative analysis of an analyte in a sample on a test strip containing a test band, a first standard band and a second standard band, comprising the steps of:
    (a) immobilizing a first calibrator agent corresponding to a first known concentration of analyte to the first standard band, and immobilizing a second calibrator agent corresponding to a second known concentration of analyte to the second standard band, wherein the calibrator agents are capable of conjugation with different label conjugates located on the standard bands, and further wherein the calibrator agents to produce a measurable response when complexed with corresponding label conjugates, (b) immobilizing an antigen in the test band capable of binding the analyte when complexed to a label conjugate, (c) contacting the test band and the standard bands with label conjugates having known concentrations of analyte and label conjugates for the calibrator agents to form two calibrator bands, and measuring a label response from the calibrator bands, (d) correlating the label responses of the calibrator bands with the label responses of known concentrations of analyte label conjugates in the test band to form a standard curve, (e) adding a sample suspected of containing an analyte, (f) adding different label conjugates sufficient to generate measurable responses in the test band when complexed with any analyte present in the sample and in the standard bands, (g) measuring the label response at the test zone and comparing the label response to the standard curve of step (d), and (h) converting the measured label responses to a concentration of analyte in the sample.

6. The method of claim 5 wherein the label generates a visual signal at the binding sites of the assay device.

7. The method of claim 5 wherein the visual signal is generated by a colloidal gold conjugate, a fluorescent dye conjugate, a latex particle conjugate or an enzyme conjugate.

8. The method of claim 5, wherein the analyte is an antigen selected from the group consisting of a virus, bacterium, fungus or a prion.

9. The method of claim 5, wherein the analyte is a hormone selected from the group consisting of hCG, thyroxin, TSH, glucagons, insulin, relaxin, prolactin, melanotropin, gastrin, somatotropin, gastrin and bradykin.

10. The method of claim 5, wherein the analyte is a cancer marker selected from the group consisting of prostate specific antigen (PSA), carcinoembryonic antigen (CEA) and alpha-fetoprotein.

11. The method of claim 5, wherein the analyte is a cardiac marker.

12. The method of claim 5 wherein the calibrator agents are monoclonal ligands.

13. The method of claim 12 wherein the calibrator agents are BTG antigens, rabbit IgG antigens and the label conjugates are label bound antibodies capable of binding to the calibrator agents.

* * * * *